United States Patent
Sakai

(10) Patent No.: US 6,327,494 B1
(45) Date of Patent: Dec. 4, 2001

(54) BODY-FAT MEASURING APPARATUS EQUIPPED WITH BODY-HEIGHT MEASURING DEVICE

(75) Inventor: Nobuya Sakai, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/492,268

(22) Filed: Jan. 27, 2000

Related U.S. Application Data

(63) Continuation of application No. PCT/JP99/02671, filed on May 21, 1999.

(30) Foreign Application Priority Data

May 25, 1998 (JP) .................................................. 10-142479
May 12, 1999 (JP) .................................................. 11-131932

(51) Int. Cl.$^7$ .................................................. A61B 5/05
(52) U.S. Cl. .................................................. 600/547
(58) Field of Search .................................................. 600/587, 595, 600/547

(56) References Cited

U.S. PATENT DOCUMENTS

| | | | |
|---|---|---|---|
| 4,911,175 | * 3/1990 | Shizgal | 600/547 |
| 5,335,667 | * 8/1994 | Cha et al. | 600/547 |
| 5,415,176 | * 5/1995 | Sato et al. | 600/547 |

FOREIGN PATENT DOCUMENTS

| | | |
|---|---|---|
| 50-86091 | 12/1948 | (JP) . |
| 61-156906 | 9/1986 | (JP) . |
| 5-49050 | 7/1993 | (JP) . |
| 5-51304 | 7/1993 | (JP) . |
| 6-189928 | 7/1994 | (JP) . |
| 6-304149 | 11/1994 | (JP) . |
| 7-12635 | 1/1995 | (JP) . |
| 7-51242 | 2/1995 | (JP) . |
| 7-75625 | 3/1995 | (JP) . |
| 7-100122 | 4/1995 | (JP) . |
| 7-303617 | 11/1995 | (JP) . |
| 9-285455 | 11/1997 | (JP) . |

* cited by examiner

Primary Examiner—Eric F. Winakur
Assistant Examiner—Pamela Wingood
(74) Attorney, Agent, or Firm—McDermott, Will & Emery

(57) ABSTRACT

An improved body-fat measuring apparatus for measuring in-vivo impedance and computing body-fat quantity can obtain accurate and stable in-vivo impedance even if hand electrodes are used for the measurement. The apparatus includes a body-height measuring device having a footstool on which a examinee mounts, a measuring terminal to contact with the top of examinee's head, and a cursor movable in upward and downward direction with holding said measuring terminal, and also includes in-vivo impedance measuring electrodes integrated with said cursor, wherein said measuring electrodes are located at a height approximately corresponding to the examinee's shoulder as said measuring terminal of said body-height measuring device contacts with the top of examinee's head so that the angle between torso region and arm region of an examinee becomes approximately right angle when the examinee grasps said measuring electrodes.

16 Claims, 2 Drawing Sheets

BODY-FAT MEASURING APPARATUS EQUIPPED WITH BODY-HEIGHT MEASURING DEVICE

REFERENCE TO RELATED APPLICATION

This Application is a continuation of International Application No. PCT/JP99/02671, whose international filing date is May 21, 1999, which in turn claims the benefit of Japanese Patent Application No. 10/142479, filed May 25, 1998, and Japanese Patent Application No. 11/131932, filed May 12, 1999 the disclosures of which Applications are incorporated by reference herein. The benefit of the filing and priority dates of the International and Japanese Applications is respectfully requested.

TECHNICAL FIELD

The present invention relates to a body-fat measuring apparatus measuring in-vivo impedance and computing body-fat quantity, more especially to a body-fat measuring apparatus equipped with a body-height measuring device.

BACKGROUND ART

In the conventional way for a body-fat measuring apparatus for measuring in-vivo impedance and computing body fat quantity, many measuring devices are proposed such as a device using a body-weight measuring device and hand/foot electrodes disclosed in Japanese Patent Publication No.5-49050 and Japanese Laid-Open Publication No.7-12635, a device using movable hand electrodes disclosed in Japanese Patent Publication No.7-51242, a device using a body-weight measuring device and foot electrodes with a body-height measuring device disclosed in Japanese Patent Laid-Open Publication No.7-100122.

When examinee's in-vivo impedance is measured by hand electrodes, it needs to keep examinee's arm region approximately at right angle to his/her torso region so as to obtain a measurement value stably, and also needs to keep the angle the same in each measurement especially for assuring the same measured quantity for every measurement. Accordingly, in the body-fat value measuring devices using hand electrodes, it is conventionally suggested to secure the hand electrode elements at a predetermined position, such as Japanese Laid-Open Publication No. 7-12635, or to keep examinee's arm region at right angle to his/her torso region himself/herself by examinee's visual adjustment, such as Japanese Patent publication No. 7-51242. However, in a type of device in which the electrode elements are secured at a predetermined position, the device is not capable of adjusting for differences in examinee's body heights so that the difference in angle between torso regions and arm regions may be extremely increased to result in making a measured value incorrect upon some examinees' measurement. Further, even if an examinee attempts to maintain an appropriate right angle position by the examinee's visual adjustment, the angle is, in fact, changed in each measurement resulting in an unstable measured value.

It is accordingly an object of the present invention to solve the above problem and to provide a device capable to obtain accurate and stable in-vivo impedance with hand electrodes, and also to provide a device for effectively utilizing in-vivo impedance measured accurately with the hand electrodes.

DISCLOSURE OF INVENTION

For solving the above problem, the present invention provide a body-height measuring device including a footstool on which an examinee mounts, a measuring terminal to contact with the top of examinee's head, and a cursor movable in upward and downward direction with holding the measuring terminal, and also provide in-vivo impedance measuring electrodes integrated with the cursor, whereby the measuring electrodes can be located at the same position in each measurement.

Furthermore, the in-vivo impedance measuring electrodes integrated with the cursor are located at a height approximately corresponding to the examinee's shoulder as the measuring terminal contacts with the top of examinee's head, whereby the angle between torso region and arm region of an examinee may be approximately right angle when the examinee grasps the measuring electrodes, in most case.

Examinee's body-height has wide difference. Since the difference between examinees in shoulder height is approximately equal to the difference of their body-height, it is assumable that the difference in shoulder height is a few ten centimeters. Thereto, the difference in height from shoulder to top of head is considerably smaller than the difference in body-height, and its individual difference is a few centimeters.

If the body-height measuring terminal of the body-height measuring device is contacted with top of head, the hand electrodes is set up so as to be located at shoulder height of a person who is average in body height so that an angle between arm region and torso region may become approximately right angle when most examinees grasp the hand electrodes, and the hand electrodes may be always set up to the same angle in every measurements when the examinee is a same person.

According to another aspect of the present invention, the apparatus of the present invention further comprises foot electrodes to contact with bottom of an examinee's foot when he/she mounts on the footstool used for body-height measurement, wherein high-frequency current applying paths and potential difference measuring areas are switched over by a controller to collect useful data for computing such as quantity of fat in each of the measuring areas.

According to further aspect of the present invention, a platform of a body-weight measuring device is used as the footstool in order to enable a single apparatus to measure body-height, in-vivo impedance, and body-weight by a series of operations.

As the result, the present invention will provide an improved apparatus to collect all of body-height, body-weight, and in-vivo impedance, that result from in-vivo impedance measurement and are included among factors such as examinee's sex, age, body-height, body-weight, and in-vivo impedance, conventionally applied to an arithmetic expression for computing a body-fat quantity, by a series of operations of a single device.

With reference to the accompanying drawings, a preferred embodiment of the present invention will be described in detail.

BEST MODE FOR CARRYING OUT THE INVENTION

Figure 1:
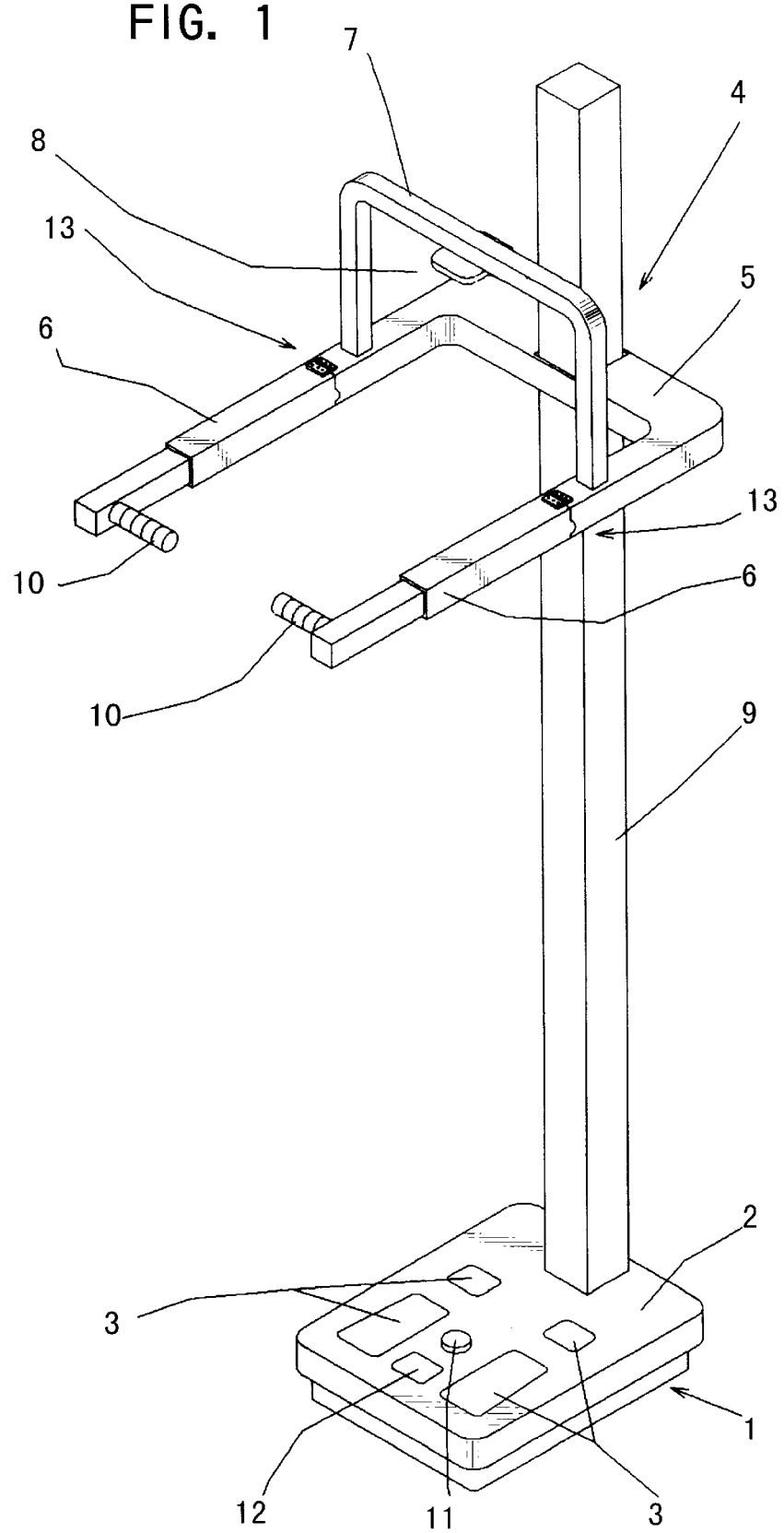
FIG. 1 is a perspective view illustrating the body-fat measuring apparatus equipped with a body-height measuring device showing as an embodiment according to the present invention.

With reference to FIG. 1, in the body-fat measuring apparatus equipped with a body-height measuring device as one embodiment according to the present invention, a platform 2 of a body-weight measuring device 1 is used as a footstool of a body-height measuring device 4 to which a columnar support 9 is fixedly attached at one of its edge side. In-vivo impedance measuring foot electrodes 3 with which the bottom of examinee's foot is contacted when the examinee mounts on there, an input device 11 setting up a power source, an information entry of personal data, and an information entry of electrode(s) to be used, and a display device 12 indicating measured or computed result(s) are provided on the surface area of the platform.

When a determination of the setting up is appointed after the information entry, such as personal data and electrode(s) to be used, with the input device have been completed, the body-weight measuring device is reset to a zero load condition for standby.

A body-height measuring device cursor 5 that slides along the columnar support 9 in upward and downward direction includes a pair of arms 6 disposed at both of right side and left side respectively, each of the arms having a grip portion at its front edge. Each of the right and left arms is made in the telescopic construction that can be expanded and contracted corresponding to the length of an examinee's arm when the examinee grasps the grip portion, and the telescopic front edge portion is swingably connected to a rear edge of the cursor through a swingable connection portion 13, the telescopic front edge portion being normally used in a specific predetermined position and also being used in flip-up motion when a examinee mounts on the platform.

An attachment member 7 connects each upper portion of the arms. A body-height measuring terminal 8 to contact with the top of examinee's head is disposed substantially in the middle of the attachment member. Hand electrodes 10 for measuring in-vivo impedance are disposed at the grip portion of each of right and left arms.

The relationship among the level of the body-height measuring terminal 8, the level of a measuring sensor (not shown) where the cursor 5 contacts with the columnar support 9 and the level of hand electrodes 10 for measuring in-vivo impedance is constantly kept in a specific relationship. The specific relationship is set up so as to make the angle between torso region and arm region of an examinee approximately right angle when the body-height measuring terminal is contacted with the top of examinee's head and the examinee grasps the hand electrodes, that is, the hand electrodes 10 for measuring in-vivo impedance is set up approximately at the height of the examinee's shoulder.

An operation process of the body-fat measuring apparatus equipped with a body-height measuring device is described as follows. An examinee enters information of physical features, such as age, sex, and electrode(s) to be used into the input device11, and then appoints a determination of the setting up by pressing the input device 11 again to make the apparatus a standby condition after the information entry.

In a automatic body-height measuring device, when the examinee mounts on the right and left foot electrodes 3,3 on the upper surface of the footstool with his/her bare feet with positioning the columnar support 9 of the body-height measuring device at the rear of his/her back, the cursor 5 located at upper portion of the columnar support is automatically started to be descended, and the cursor is continued to be descend until the body-height measuring terminal 8 will be contacted with the top of the examinee's head. When the terminal is contacted with the top of his/her head, a sensor (not shown) disposed in the terminal detects that the terminal is contacted with the top of his/her head so that the decent of the cursor may be stopped and also the in-vivo impedance measuring hand electrodes 10,10 may be stopped at the height of his/her shoulder, and at this moment the preparation for body-height and body-weight measurement is completed.

Since the angle between arm region and torso region of the examinee becomes approximately right angle when the examinee grasps the in-vivo impedance measuring electrodes disposed in front of the examinee's shoulder with both hands, his/her in-vivo impedance is measured when the electrodes are properly grasped.

The examinee's body-height, body-weight, and in-vivo impedance are sequentially measured, and these measured values and pre-entered information such as sex and age are then applied to an arithmetic expression to compute fat quantity, etc., The measured results and the computed result(s) are then sequentially indicated on the display device 12. When every measured value and computed result(s) have been finished to indicate, a signaling device (shown in FIG. 2) then informs the completion of the measurement and computation, at this moment the process is completed.

The measurement of body-height is started just after the body-height measuring terminal is contacted with the top of the examinee's head even if the examinee does not grasp the hand electrodes, and also the measurement of body-weight is started when the examinee stops his/her motion on the platform and the apparatus then determines that the body-weight measurement can be performed without trouble even if the examinee does not grasp the hand electrodes.

In a manual type body-height measuring device, when a examinee who mounts on the platform pulls down the hand electrodes of the cursor located upper position of the columnar support, the sensor in the terminal detects that the top of the examinee's head contacts with the terminal to inform the contact with a signal unit such as buzzer sound. When the examinee stops to pull down the hand electrodes responsive to the signal, the measurement of body-height, body-weight, and in-vivo impedance is started.

A processor (cf. control, computation and memory device shown in FIG. 2) performs an operation by use of the arithmetic expression and the information such as examinee's physical data and electrode(s) to be used which was entered from the input device, the body-weight data that was measured by the body-weight measuring device, the body-height data that was measured by the body-height measuring device, and the in-vivo impedance data that was measured by the in-vivo impedance measuring device, and then indicates the measured body-height, the measured body-weight, the computed body-fat quantity, etc. by the display device 12.

Figure 2:
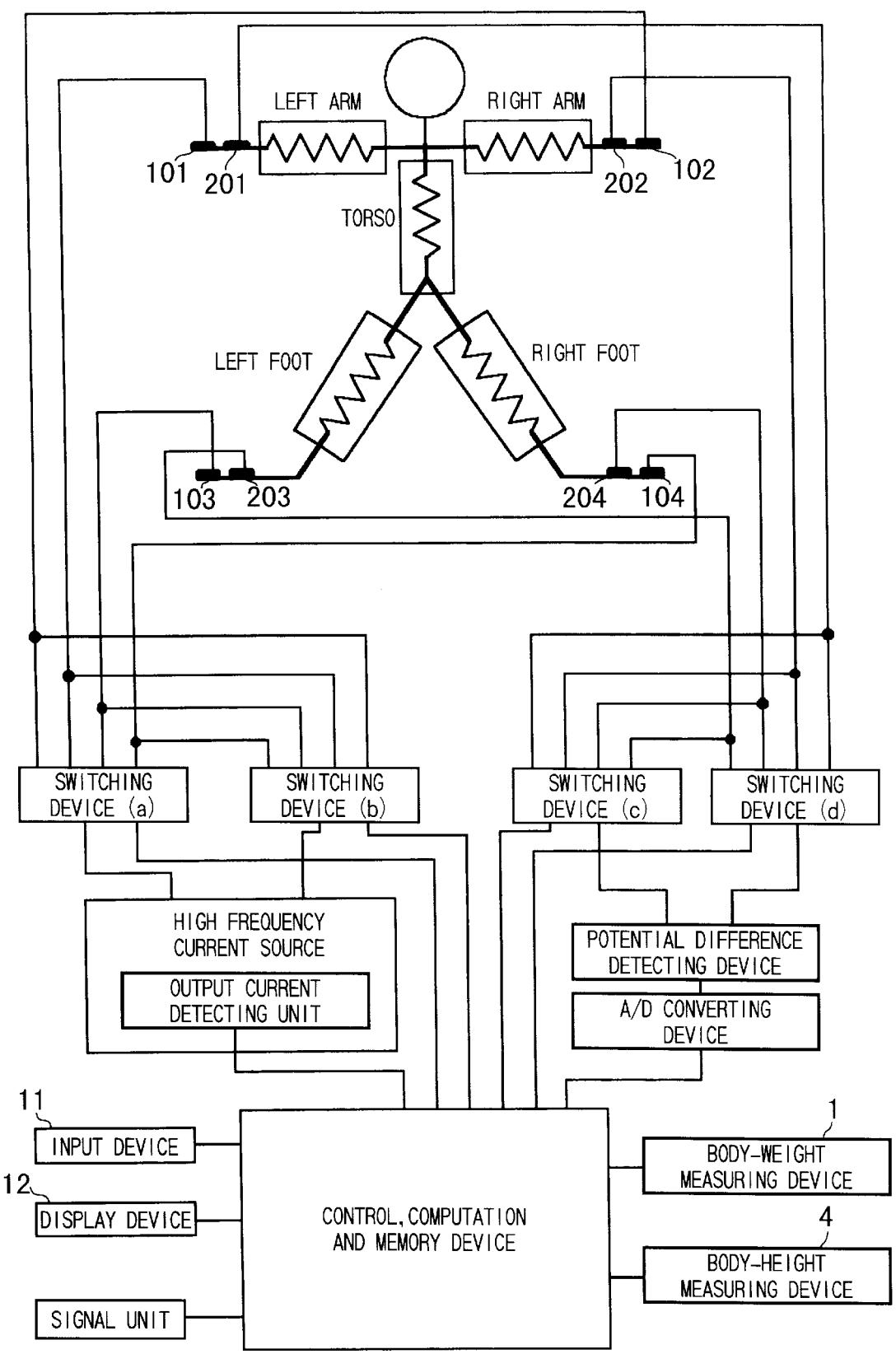
FIG. 2 is a block diagram illustrating an example of the circuitry of the body-fat measuring apparatus equipped with a body-height measuring device shown in FIG. 1.

With reference to FIG. 2, the switching circuitry of the electrode(s) to be used for measurement of the in-vivo impedance measuring device is described.

According to FIG. 2, the reference numerals 101, 201, 102, and 202 indicate the hand electrodes 10 that may be contacted with examinee's palms when he/her grasps them by both hands in FIG. 1, and the reference numerals 103, 203, 104, and 204 indicate the foot electrodes that may be contacted with bottom of examinee's foot when he/she mounts on the platform in FIG. 1.

The reference numerals 101, 102, 103, and 104 indicate electrodes for applying high frequency electric current, and the reference numerals 201, 202, 203, and 204 indicate electrodes for measuring potential difference.

A switching device (a) and a switching device (b) switch the high frequency current applying electrodes to a high frequency electric current source associated with an output current detecting unit in order to select a current path, and a switching device (c) and a switching device (d) switch the potential difference measuring electrodes to a potential difference detecting device associated with an A/D converting device in order to select potential difference measuring areas.

When the high frequency current applying electrodes 101 and 102, and the potential difference measuring electrodes 201 and 202 are respectively selected, the impedance of the examinee's upper body is measured. When the high frequency current applying electrodes 103 and 104, and the potential difference measuring electrodes 203 and 204 are respectively selected, the impedance of the examinee's lower body is measured. The fat quantity is presumed on the basis of each of the measured in-vivo impedance values.

In such apparatus according to the present invention that includes hand electrodes being respectively contacted with both of the examinee's palms and foot electrodes being respectively contacted with both of bottoms of the examinee's feet so as to enable respectively to collect accurate in-vivo impedance values, the in-vivo impedance of the examinee's left foot is measured when the high frequency current applying electrodes 103 and 104, and the potential difference measuring electrodes 201 and 203 are respectively selected, and the in-vivo impedance of the examinee's right foot is also measured when the high frequency current applying electrodes as same as the above, and the potential difference measuring electrodes 201 and 204 are respectively selected. Thus, the difference between the muscle quantities of the examinee's right and left feet can be learnt by means of switching the potential difference measuring electrodes with using the same current path so that the degree of progress of the rehabilitation on bone fracture .may be checked.

Additionally, the in-vivo impedance of the examinee's torso is measured when the high frequency current applying electrodes 101 and 103, and the potential difference measuring electrodes 202 and 204 are respectively selected so that the amount of fat in abdominal region as being a very important factor for health management can be accurately measured.

Effect of the Invention

When the body-height measuring terminal is contacted with the top of examinee's head and the preparation for the body-height measurement is completed, the angle between torso region and arm region of an examinee becomes approximately right angle when the examinee grasps the in-vivo impedance measuring electrodes by his/her both hands and also each measurement can be performed with the same angle so that accurate and stable measured value can be obtained at all times.

Furthermore, since the foot electrodes and hand electrodes can be selectively switched to perform accurate measurement for different body regions, fat quantity of each body region can be measured efficiently and accurately.

Additionally, since the hand electrodes are disposed at the existing cursor of the body-height measuring device, any additional securing device for the hand electrodes is unnecessary.

What is claimed is:

1. An in-vivo impedance measuring apparatus comprising:
    a body-height measuring device including
        (1) a footstool on which an examinee mounts,
        (2) a measuring terminal to contact with the top of examinee's head, and
        (3) a cursor movable in upward and downward direction in conjunction with said measuring terminal; and
    in-vivo impedance measuring hand electrodes integrated with said cursor, whereby in-vivo impedance is measured when an examinee grasps said electrode by hand.

2. An in-vivo impedance measuring apparatus according to claim 1, said hand electrodes integrated with said cursor of said body-height measuring device comprise two sets of electrodes to contact with each of palms of right and left hand of an examinee respectively.

3. An in-vivo impedance measuring apparatus according to claim 1, wherein said hand electrode integrated with said cursor comprise a pair of electrodes including of a high frequency current applying electrode and a potential difference measuring electrode.

4. An in-vivo impedance measuring apparatus according to claim 1, wherein said in-vivo impedance measuring hand electrodes are located at a height approximately corresponding to the examinee's shoulder as said measuring terminal of said body-height measuring device contacts with the top of an examinee's head.

5. An in-vivo impedance measuring apparatus according to claim 1, wherein said in-vivo impedance measuring hand electrodes are swingable to said cursor.

6. An in-vivo impedance measuring apparatus according to claim 1, wherein said footstool of said body-height measuring device further includes a platform of a body-weight measuring device.

7. An in-vivo impedance measuring apparatus comprising:
    (A) a body-height measuring device including
        (1) a footstool on which an examinee mounts,
        (2) a measuring terminal to contact with the top of examinee's head, and
        (3) a cursor movable in upward and downward direction in conjunction with said measuring terminal,
    (B) hand electrodes integrated with said cursor,
    (C) foot electrodes integrated with said footstool, and
    (D) a control device for computing in-vivo impedance with said hand electrodes and said foot electrodes.

8. An in-vivo impedance measuring apparatus according to claim 7, wherein said hand electrodes are located at a height approximately corresponding to the examinee's shoulder as said measuring terminal of said body-height measuring device contacts with the top of an examinee's head.

9. An in-vivo impedance measuring apparatus according to claim 7, wherein said hand electrodes are swingable to said cursor.

10. An in-vivo impedance measuring apparatus according to claim 7, wherein said footstool of said body-height measuring device includes a platform of a body-weight measuring device.

11. An in-vivo impedance measuring apparatus according to claim 7, wherein said control device includes a switching means for switching the connection of said hand electrode and said foot electrode.

12. An in-vivo impedance measuring apparatus according to claim 5, wherein foot electrodes integrated with said footstool of said body-height measuring device comprise two sets of foot electrodes to contact with each of the bottoms of right and left feet respectively.

13. An in-vivo impedance measuring apparatus according to claim 7, wherein said foot electrodes integrated with said footstool of said body-height measuring device comprise a pair of electrodes including a high frequency current impressing electrode and a potential difference measuring electrode.

14. An in-vivo impedance measuring apparatus comprising:
   (A) a body-height measuring device including
      (1) a footstool on which an examinee mounts,
      (2) a measuring terminal contacted with the top of examinee's head, and
      (3) a cursor
         (a) movable in upward and downward direction in conjunction with holding said measuring terminal, and
         (b) located at a height approximately corresponding to an examinee's shoulder as said measuring terminal of said body-height measuring device contacts with the top of an examinee's head.
   (B) hand electrodes integrated with said cursor,
   (C) foot electrodes integrated with said footstool, and
   (D) a control device
      (a) for switching and connecting electrodes applied to said hand electrodes and said foot electrodes, and
      (b) for computing in-vivo impedance.

15. An in-vivo impedance apparatus comprising:
   (A) a body-height measuring device including
      (1) a footstool on which an examinee mounts,
      (2) a measuring terminal to contact with the top of examinee's head, and
      (3) acursor
         (a) movable in upward and downward direction in conjunction with holding said measuring terminal, and
         (b) located at a height approximately corresponding to the examinee's shoulder as said measuring terminal of said body-height measuring device is contact with the top of examinee's head.
   (B) hand electrodes
      (1) including a pair of electrodes including a high frequency current applying electrode and a potential difference measuring electrode integrated with said cursor, and
      (2) having two sets of said pair of electrodes to independently contact with each of palms of both hands.
   (C) foot electrodes
      (1) including a pair of electrodes including a high frequency current applying electrode and a potential difference measuring electrode integrated with said footstool, and
      (2) having two sets of said pair of electrodes to independently contact with each of bottoms of both feet, and
   (D) a control device for controlling switching of said hand electrodes and said foot electrodes, and computing in-vivo impedance.

16. An in-vivo impedance measuring apparatus comprising:
   (A) a body-height measuring device including
      (1) a footstool on which an examinee mounts
         (a) being a platform of a body-weight measuring device,
      (2) a measuring terminal to contact with the top of examinee's head, and
      (3) a cursor
         (a) movable in upward and downward direction in conjunction with holding said measuring terminal, and
         (b) located at a height approximately corresponding to the examinee's shoulder as said measuring terminal of said body-height measuring device contacts with the top of examinee's head.
   (B) hand electrodes
      (1) including a pair of electrodes including a high frequency current applying electrode and a potential difference measuring electrode integrated with said cursor, and
      (2) having two sets of said pair of electrodes to independently contact with each of palms of both hands.
   (C) foot electrodes
      (1) including a pair of electrodes including a high frequency current applying electrode and a potential difference measuring electrode integrated with said footstool, and
      (2) having two sets of said pair of electrodes to independently contact with each of bottoms of both feet, and
   (D) a control device for controlling switching of said hand electrodes and said foot electrodes, and computing in-vivo impedance.

* * * * *